United States Patent [19]
Kitajima

[11] Patent Number: 5,186,194
[45] Date of Patent: Feb. 16, 1993

[54] PROBE WASHING VESSEL

[75] Inventor: Masaichi Kitajima, Tokyo, Japan

[73] Assignee: Olympus Optical Co., Ltd., Tokyo, Japan

[21] Appl. No.: 748,276

[22] Filed: Aug. 21, 1991

[30] Foreign Application Priority Data

Aug. 24, 1990 [JP] Japan ................... 2-223616

[51] Int. Cl.$^5$ .................. B08B 3/04; B08B 9/08
[52] U.S. Cl. .................... 134/154; 73/864.22; 134/155; 134/164; 134/170; 134/182
[58] Field of Search ............ 134/104.2, 135, 147, 134/154, 155, 164, 170, 182, 186; 422/292; 4/198, 199, 200, 201, 202, 206, 207, 651; 141/86, 88, 311 A; 73/864.22; 220/746

[56] References Cited

U.S. PATENT DOCUMENTS

| | | | |
|---|---|---|---|
| 1,783,390 | 12/1930 | Robertson | 134/147 |
| 4,730,631 | 3/1988 | Schwartz | 134/155 |
| 4,817,443 | 4/1989 | Champseix et al. | 134/170 X |
| 4,989,623 | 2/1991 | Hoffman et al. | 134/170 X |

FOREIGN PATENT DOCUMENTS

| | | | |
|---|---|---|---|
| 0290006 | 11/1988 | European Pat. Off. | |
| 1621604 | 9/1970 | Fed. Rep. of Germany | 134/186 |
| 0144165 | 12/1978 | Japan | 134/186 |
| 12873 | 5/1896 | United Kingdom | 4/200 |

OTHER PUBLICATIONS

Patent Abstracts of Japan, vol. 12, No. 114, Apr. 1988 Nippon Tectron Co., Ltd., Cleaning Device or Probe.
Patent Abstracts of Japan, vol. 012, No. 383, Oct. 1988 Toshiba Corp., Probe Cleaning Tank.

*Primary Examiner*—Philip R. Coe
*Attorney, Agent, or Firm*—Frishauf, Holtz, Goodman & Woodward

[57] ABSTRACT

A probe washing vessel for sucking in and dispensing blood plasma, blood cells, blood serum, or body fluid and the like comprises a washing reservoir, a washing chamber in a form of a hole which formed in the washing reservoir and in which a probe is inserted, and a bypass flow path formed in the washing reservoir and having one end communicating with the washing chamber and the other end opened to the atmosphere.

14 Claims, 4 Drawing Sheets

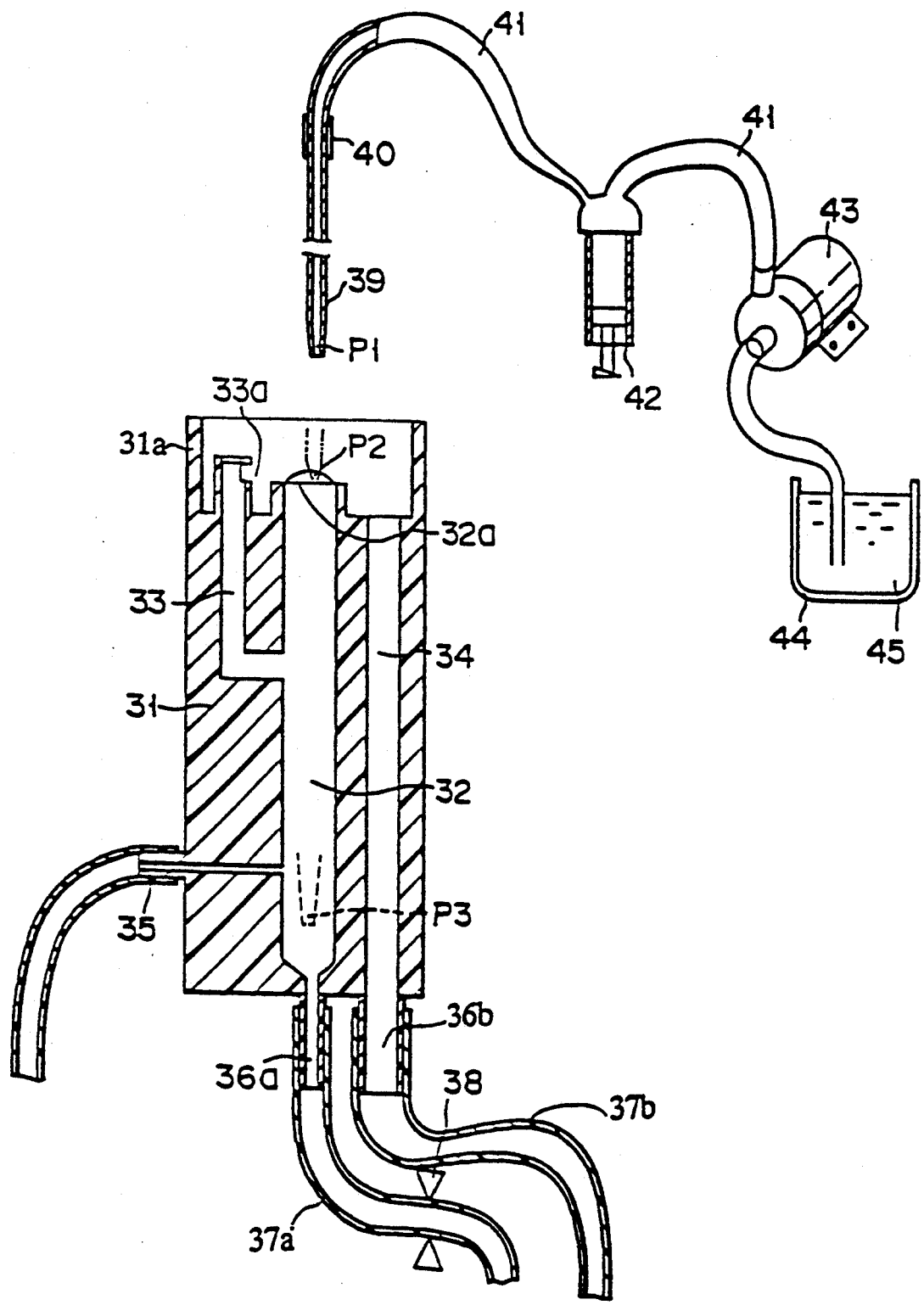
F I G. 1

PROBE WASHING VESSEL

BACKGROUND OF THE INVENTION

1. Field of the Invention

This invention relates to an improvement of a probe washing vessel for washing probes which suck in and dispense blood plasma, blood cells, blood serum, or body fluid.

2. Description of the Related Art

As is known well, probes have been used for sucking in and dispensing blood plasma, blood cells, blood serum, or body fluid. Conventionally, the outer wall of such a probe has been washed by filling the washing chamber 2 of a washing reservoir 1 with washing water 3 or by inserting the probe 4 into the washing chamber 2 from which water is overflowing, as shown in FIG. 3. An inlet 5 of washing water communicates with the washing chamber 2.

In order to wash the inner wall of the probe 4, water is poured into the probe 4 such that dirt attached on the inner wall of the probe is washed away by the force of the washing water. When the inner wall is washed in case of the prove 4 is inserted in the washing chamber 2 as shown in FIG. 4 in this case, washing water discharged from the tip of the probe 4 flows the space between the outer wall of the probe and the inner wall of the washing chamber 2 and overflows from the washing chamber 2. In this way, the outer wall of the probe can also be washed.

As shown in FIG. 5, water for washing the inner wall of the probe 4 (hereinafter referred to as "inner-wall washing water") is poured into the washing chamber after the probe 4 has reached the lowest position P of the probe 4 in the washing water in the washing chamber 2. Thus, the inner wall of the probe 4 is not washed while the probe 4 is being moved from the highest position Q to the lowest position P. If, however, inner-wall washing water can be poured into the washing chamber 2 at the position Q, the inner wall can also be washed while the probe 4 is lifted from the position Q to the position P. Accordingly, the time for washing the inner wall is increased and carry-over is reduced.

Since, however, water for washing the outer wall of the probe 4 (hereinafter referred to as "outer-wall washing water") is filled in the washing chamber 2 or overflows from it in the conventional groove washing vessel, the inner-wall washing water hits against the outer-wall washing water and splashes out of the washing reservoir 1. Thus, the inner-wall washing water cannot be used in this state. More specifically, since the inner wall washing water 6 is discharged from the hole formed in the probe tip, which hole has an inner diameter of substantially 0.5 to 0.7 mm, the inner-wall washing water strongly hits against the outer-wall washing water 3 and jumps very highly (see FIG. 6).

SUMMARY OF THE INVENTION

The object of this invention is to provide a probe washing vessel which can remarkably reduce the splashing of washing water for washing the inner wall of a probe, which hits against washing water for washing the outer wall of the probe, by providing a bypass flow path at an intermediate portion of a probe washing hole.

According to this invention, a probe washing vessel for sucking in and dispensing blood plasma, blood cells, blood serum, or body fluid comprises a washing reservoir for containing washing water, a washing reservoir in a form of a hole formed in the washing reservoir for having a probe inserted therein, a bypass flow path communicating with the washing chamber and having one end opened to the atmosphere.

As shown in FIG. 7, a probe washing vessel of this invention has a bypass flow path 13 formed at an intermediate portion of the probe washing hole or the probe washing chamber 12 in a washing reservoir 11, whereby water 15 for washing the inner wall of a probe 14 (or inner-wall washing water 15) discharged from the hole formed in the tip of the probe 14 can be remarkably prevented from jumping from water 16 for washing the outer wall of the probe 14 (or outer-wall washing water 16), when the inner wall washing water 15 hits against the outer wall washing water 16.

More specifically, pressure generated by the hitting of the inner-wall washing water 15 discharged from the probe tip against the outer-wall washing water 16 filled in the probe washing hole 12 escapes to the bypass path 13. This structure facilitates a remarkable reduction of the splashing of the washing water 15 out of the washing reservoir, which splashing unavoidably occurs in the conventional probe washing vessel because there is no place from which the pressure escapes. In other words, by releasing the pressure generating at the time of hitting of the water 15 against the water 16 into the bypass flow path 13, part of the inner-wall washing water and part of outer-wall washing water flow through the bypass flow path 13 and are exhausted in a lateral direction from a hole as shown in FIG. 7. In general, the bypass flow path 13 is shaped so as to extend along the washing chamber 12 but it is not limited thereto.

In this invention, the outlet of the bypass flow path may be directed upward or laterally. It is preferable, however, that it is directed toward the opening of the washing hole of the washing reservoir. The amount of washing water increases at the opening end of the washing hole and is likely to splash out of the washing reservoir. When the outlet of the bypass flow path is directed toward the opening of the washing hole of the washing reservoir, washing water discharged from the outlet of the bypass flow path is prevented from being greatly splashed out of the opening of the washing hole. Therefore, by using this bypass flow path, the height of the outer wall of the washing reservoir can be made low.

This invention fundamentally comprises a washing chamber in a form of a chamber which formed in a washing reservoir containing washing water and into which a probe is inserted, and a bypass flow path having one end communicating with the washing chamber and th other end opened to the atmosphere. A water exhaust hole is formed in the washing reservoir so as to extend in the direction of the axis of the washing chamber, an inlet for outer wall washing water is rendered to communicate with the lowest portion of the washing chamber, and outlets are provided so as to communicate with the washing chamber and the water exhaust hole. This structure can enhance washing efficiency of the probe. The outlets of the washing chamber and the water exhaust hole are formed under the inlet of outer-wall washing water in order to improve the water exhaust efficiency.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a general view illustrating a probe washing vessel according to one embodiment of this invention;

DETAILED DESCRIPTION OF THE PREFERRED EMBODIMENTS

Figure 2:
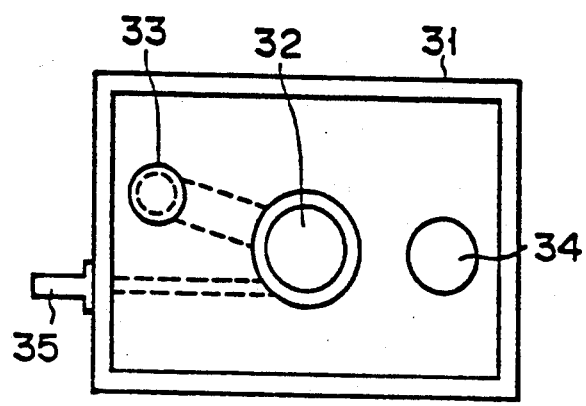
FIG. 2 is a plan view of the washing reservoir of the washing vessel in FIG. 1.
Figure 3:
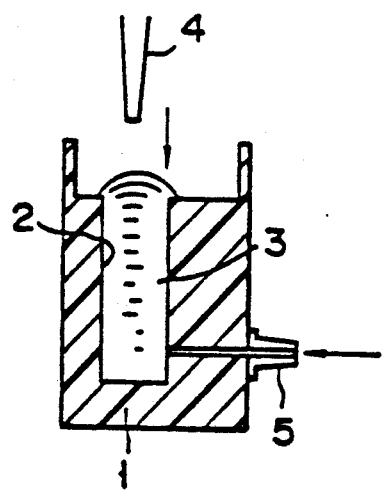
FIG. 3 is a cross-sectional view of the conventional washing vessel, illustrating how to wash the outer wall of a probe.
Figure 4:
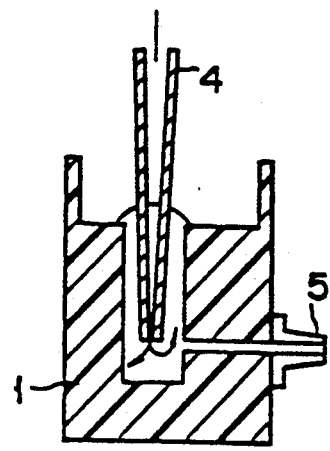
FIG. 4 is a cross-sectional view of the conventional washing vessel, showing how to wash the inner wall of a probe.
Figure 5:
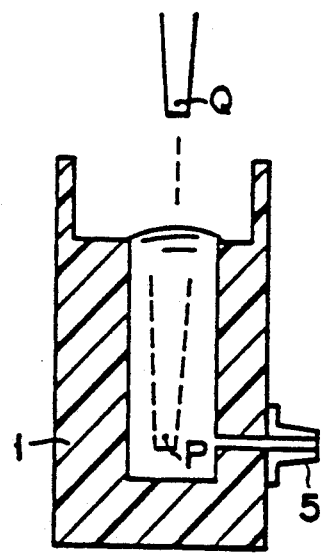
FIG. 5 is a cross-sectional view of the conventional washing vessel, illustrating why the inner wall of a probe cannot be washed when the probe is disposed between the highest position Q and the lowest position P.
Figure 6:
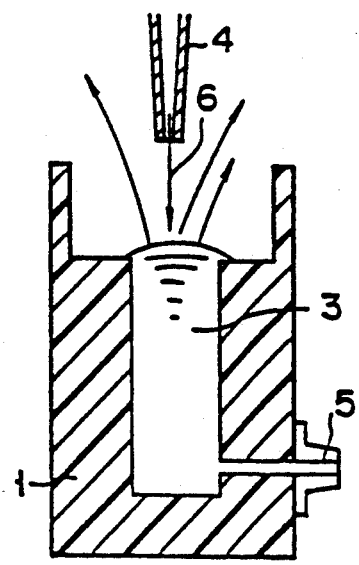
FIG. 6 is a cross-sectional view of the conventional washing vessel, illustrating why the inner-wall washing water jumps very highly when it strongly hits against the outer-wall washing water.
Figure 7:
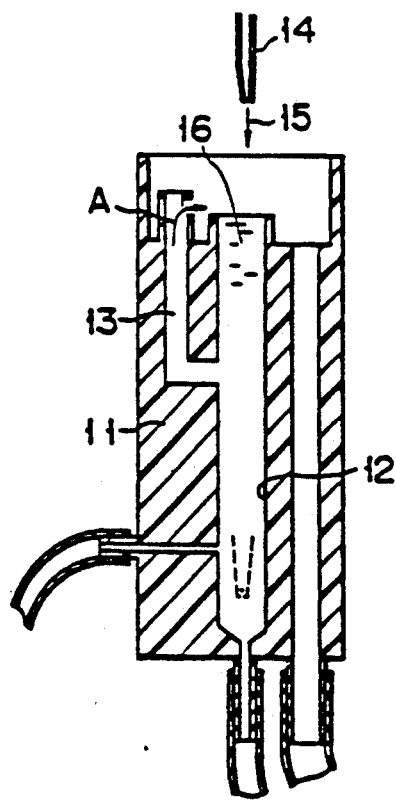
FIG. 7 is a cross-sectional view illustrating the operation of the washing vessel according to this invention.

Referring to FIG. 1, an embodiment of a probe washing vessel according to this invention will now be explained in detail.

A probe washing reservoir 31 made of vinyl chloride is substantially cylindrical and is used for containing water for washing probes. A probe washing chamber (or a probe chamber in a form of a hole) 32 is provided so as to extend through the central portion of the probe washing reservoir 31 along its axis. Formed in the washing reservoir 31 is a bypass flow path 33 having one end communicating with the washing chamber 32 and the other end opened to the atmosphere. The bypass path 33 is used for releasing impulses caused by the hit of inner-wall washing water against outer wall washing water, and its outlet 33a is directed laterally (more specifically, directed toward the opening of the washing chamber 32) such that water does not jump up too highly.

An overflow water exhaust hole 34 for exhausting overflowing washing water extends vertically along the washing chamber 32 in the washing reservoir 31. A washing water inlet 35 is formed in a lowest portion of the wall of the washing reservoir 31 so as to communicate with the washing chamber 32. A pump (not shown) is connected to the washing water inlet 35, for supplying washing water from a tank (not shown) to the chamber 32. Water outlets 36a and 36b communicate with the washing chamber 32 and the exhaust hole 34, respectively. Hoses 37a and 37b made of vinyl chloride are connected to the exhaust water outlets 36a and 36b, respectively. A pinch valve 38 is provided at an intermediate portion of the hose 37a.

An outer wall 31a forming an upper portion of the washing reservoir 31 is made higher than the outlet of the bypass flow path 33 such that washing water from the outlet 33a of the bypass flow path 33 does not splash out of the washing reservoir 31. When the outlet 33a is not directed upward but laterally, unlike this invention, the outlet 33a must be higher than the outlet of this embodiment.

A probe 39 disposed over the probe washing vessel constructed as explained above is washed or cleaned, as described below. A tube 41 is connected to the probe 39 by means of a rubber tube 40. The tube 41 is connected at its intermediate portion to a sample dispensing syringe 42 and is connected via a pump 43 to a tank 44 containing washing water 45. The probe 39 can be moved up and down by means of moving means and circuits and the like (not shown). The probe 39 is located at the highest position $P_1$ right over the opening of the washing chamber 32 before washing, at a washing starting position $P_2$ at the opening of the washing chamber when washing water starts to flow and at the lowest position $P_3$ at the bottom portion of the opening of the washing chamber 32 and is moved between the highest position and the lowest position.

The operation of the embodied probe washing vessel will now be explained.

(1) After sucking in or dispensing a sample, the probe 39 stops over the washing chamber 32 and the washing operation of the probe starts. First, probe outer-wall washing water is poured from the washing water inlet 35 into the washing chamber 32 by means of the pump (not shown) until the water reaches the top end (the open end or opening) 32a of the washing chamber 32. Since the outlet 33a of the bypass flow path 33 is at the same level as the top end 32a of the washing chamber 32, water for washing the outer wall 38a of the probe 39 also reaches the outlet 33a. In this state, the pinch valve 38 is closed and thus washing water does not flow out of the washing chamber 32 through the washing water outlet 36a.

(2) After the washing chamber 32 is filled with outer-wall washing water, inner-wall washing water is poured by the pump 43 in the inner wall of the probe which is disposed at the position $P_1$, whereby washing or cleaning of the inner wall starts. The inner diameter of the tip of the probe 39 is substantially 0.5 to 0.7 mm. The inner-wall washing water discharged at the position $P_1$ hits against the outer-wall washing water filled in the washing chamber 32 and reaches its opening 32a. If the bypass flow path 33 is not provided as in the conventional case the washing water splashes to a position higher than the opening of the washing hole. In this embodiment according to this invention, however, the pressure generated by the hit of inner wall against inner wall washing water escapes through the bypass flow path 33 in the lateral direction, that is, from the outlet 33a toward the above-mentioned opening. The outer wall washing water is continuously poured from the inlet 35 into the washing chamber 32, and, at the same time, the inner wall washing water is continuously discharged from the tip end of the probe. During this continuous flow of both types of washing water, the probe 39 is lowered in the washing chamber 32 from the highest position $P_1$ to the lowest position $P_3$ at the bottom portion of the washing chamber 32, and then the probe 39 is lifted to the original highest position $P_1$. In such a way, the probe 39 is washed or cleaned. The supplied water drops naturally from the water exhaust hole 34 and is exhausted to the outside of the washing reservoir 31 through the water outlet 36. After the probe 39 has returned to the highest position P₁, the pinch valve 38 is opened and the washing water in the washing chamber 32 is exhausted from the washing water outlet 36a to the outside of the washing reservoir 31.

The longer the time during which washing water is sucked in or dispensed, the higher the washing efficiency. In the conventional probe washing vessel, when the tip of the probe 39 is at the level between the highest position P₁ and the top end (opening) 32a of the washing chamber 32, inner wall washing water discharged from the probe strongly hits against the outer wall washing water, and jumps very highly so as to splash out of the washing reservoir. Thus, it is unable to discharge inner-wall washing water from the probe when the probe is located between the above-mentioned positions. In this invention, however, inner-wall washing water dropping on outer wall washing water does not jump very highly even when the probe is disposed between these positions and, therefore, the inner wall of the probe can be washed or cleaned during the time when the probe is between the above-mentioned positions. Accordingly, in this invention, the inner wall of a probe can be washed or cleaned during not only the time in which the probe 30 is inserted in the washing hole 38 but also the time in which the probe 30 is lowered from the highest position to the lowest position and then lifted to the original highest position, whereby the washing efficiency of the inner wall of a probe is increased.

The outlet of the bypass flow path is directed toward the opening of the washing hole in the above-mentioned embodiment but is not limited thereto. Although the upper wall of the washing reservoir is made a little higher than that of the embodiment as shown in FIG. 1, the outlet of the bypass flow path may be directed upward. In this case, diameter of the washing reservoir can be made smaller than that of the embodiment as shown in FIG. 1.

The washing reservoir is cylinder in the embodiment but it is not limited thereto. It may have a square pillar shape.

The washing reservoir and hoses are not always made of vinyl chloride but of other material.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A probe washing vessel for washing inside and outside portions of probes that suck in and dispense at least one of blood plasma, blood cells and blood serum, the probe washing vessel comprising:
   a washing reservoir for storing a washing water;
   a washing chamber in said washing reservoir for receiving a probe therein and for washing an outside portion of said probe, said washing chamber being elongated in a vertical direction thereof;
   a bypass flow path for preventing said washing water from splashing, when said probe is positioned at a first position that is vertical above said washing chamber and when said vessel is viewed in a vertical position thereof, and wherein an additional washing water flows through and washes an inner wall of said probe, said additional washing water colliding with a surface of a quantity of said washing water that is already within said washing chamber;
   a washing water exhaust aperture in said washing reservoir, for exhausting an overflow of washing water from said washing reservoir;
   a washing water inlet port for supplying said washing water into said washing chamber and for washing said outside portion of said probe, said washing water inlet port being formed in a lower end portion of said washing reservoir, and said washing water inlet port being in fluid communication with said washing chamber;
   a first washing water exhaust outlet port at a lower end portion of said washing chamber; and
   a second washing water exhaust outlet port at a lower end portion of said washing reservoir, said second washing water exhaust outlet port being in fluid communication with said washing water exhaust aperture.

2. The vessel according to claim 1, wherein:
   a first aperture is provided in said washing chamber; and
   a first end portion of said bypass flow path includes an outlet portion thereof, that is directed toward said first aperture of said washing chamber, said bypass flow path having a second end portion thereof that is in fluid communication with said washing chamber.

3. The vessel according to claim 2, wherein said first end portion of said bypass flow path is positioned to be on a common level with said first aperture of said washing chamber, when said vessel is viewed in said vertical position thereof.

4. The vessel according to claim 3, wherein said first washing water exhaust outlet port and said second washing water exhaust outlet port are positioned to be below said washing water inlet port, when said vessel is viewed in said vertical position thereof.

5. The vessel according to claim 2, wherein said washing water exhaust aperture is at a level below said common level of said first aperture of said washing chamber and said first end portion of said bypass flow path, when said vessel is viewed in said vertical position thereof.

6. The vessel according to claim 1, further comprising means for closing said first washing water exhaust outlet port, when washing water is supplied into said washing chamber through said washing water inlet port.

7. The vessel according to claim 1, further comprising means for continuously providing said additional washing water to said probe.

8. A probe washing vessel for washing inside and outside portions of probes that suck in and dispense at least one of blood plasma, blood cells and blood serum, the probe washing system comprising:
   a washing reservoir for storing a washing water;
   a washing chamber in said washing reservoir for receiving a probe therein and for washing an outside portion of said probe, said washing chamber being elongated in a vertical direction thereof;
   said probe being cyclically movable from a first position vertically above said washing chamber, when said washing chamber is viewed in a vertical position thereof, to a second position in said washing chamber, where washing of said outside portion of said probe occurs;

a bypass flow path for preventing said washing water from splashing, when said probe is positioned at said first position;

a washing water exhaust aperture in said washing reservoir, for exhausting an overflow of washing water from said washing reservoir;

a washing water inlet port for supplying said washing water into said washing chamber and for washing said outside portion of said probe, said washing water inlet port being at a lower end portion of said washing reservoir, and said washing water inlet port being in fluid communication with said washing chamber;

means for providing an additional washing water to said probe, said additional washing water flowing through and washing an inner wall of said probe, said additional washing water colliding with a surface of a quantity of washing water that is already within said washing chamber;

a first washing water exhaust outlet port at a lower end portion of said washing chamber; and a second washing water exhaust outlet port at a lower end portion of said washing reservoir, said second washing water exhaust outlet port being in fluid communication with said washing water exhaust aperture.

9. The probe washing system according to claim 8, wherein:

a first aperture is provided in said washing chamber; and a first end portion of said bypass flow path includes an outlet portion thereof, that is directed toward said first aperture of said washing chamber, said bypass flow path having a second end portion thereof that is in fluid communication with said washing chamber.

10. The probe washing system according to claim 9, wherein said first end portion of said bypass flow path is positioned to be on a common level with said first aperture of said washing chamber, when said washing chamber is viewed in said vertical position thereof.

11. The probe washing system according to claim 10, wherein said first washing water exhaust outlet port and said second washing water exhaust outlet port are positioned to be below said washing water inlet port, when said washing chamber is viewed in said vertical position thereof.

12. The probe washing system according to claim 10, wherein said washing water exhaust aperture is at a level below said common level of said first aperture of said washing chamber and said first end portion of said bypass flow path, when said washing chamber is viewed in said vertical position thereof.

13. The probe washing system according to claim 8, further comprising means for closing said first washing water exhaust outlet port when washing water is supplied into said washing chamber through said washing water inlet port.

14. The probe washing system according to claim 8, wherein said means for providing said additional washing water to said probe, continuously supplies said washing water to said probe, as said probe is being washed.

* * * * *